United States Patent
Lin et al.

(10) Patent No.: US 9,774,773 B2
(45) Date of Patent: Sep. 26, 2017

(54) MARKING APPARATUS AND MARKING METHOD FOR DISPLAY PANEL

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Zijin Lin, Beijing (CN); Chaoyang Deng, Beijing (CN); Chao Tian, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 228 days.

(21) Appl. No.: 14/500,189

(22) Filed: Sep. 29, 2014

(65) Prior Publication Data

US 2015/0262350 A1    Sep. 17, 2015

(30) Foreign Application Priority Data

Mar. 11, 2014   (CN) .......................... 2014 1 0088236

(51) Int. Cl.
  *H04N 5/225*    (2006.01)
  *G02B 13/00*    (2006.01)
  *G01N 21/88*    (2006.01)

(52) U.S. Cl.
  CPC ....... *H04N 5/2254* (2013.01); *G01N 21/8851* (2013.01); *G02B 13/0015* (2013.01); *G01N 2021/888* (2013.01); *G01N 2021/8861* (2013.01)

(58) Field of Classification Search
  CPC ................ G09G 3/006; H04N 5/2254; G01N 2021/8861; G01N 2021/888; G01N 21/8851
  USPC ........................................... 348/87
  See application file for complete search history.

(56) References Cited

U.S. PATENT DOCUMENTS

| 5,995,137 A * | 11/1999 | Yamada ............... G01N 21/956 348/241 |
| 2002/0139273 A1* | 10/2002 | Murata .................... B41J 11/46 101/484 |
| 2007/0117225 A1* | 5/2007 | Capaldo ............. G01N 21/8806 438/14 |

(Continued)

*Primary Examiner* — Jamie Atala
*Assistant Examiner* — Ayman Abaza
(74) *Attorney, Agent, or Firm* — Nath, Goldberg & Meyer; Joshua B. Goldberg; Annie J. Kock

(57) ABSTRACT

The present invention provides a marking apparatus for a display panel and a marking method for a display panel. The marking device comprises an image acquiring module, a simulated marking module and a real marking module. A simulated marking line is drawn, by the simulated marking module, in an image acquired by the image acquiring module, of a region containing a position where a defect occurs on a display panel to be marked. The real marking module automatically draws a real marking line on the display panel to be marked according to the simulated marking line. Thus, a position where a defect occurs on a display panel to be marked is accurately marked, and it is convenient for an engineer to accurately locate and sample the defective position in the subsequent analysis process.

17 Claims, 3 Drawing Sheets

(56) References Cited

U.S. PATENT DOCUMENTS

| | | | |
|---|---|---|---|
| 2014/0146163 A1* | 5/2014 | Woo | G01N 21/8901 348/88 |
| 2014/0268105 A1* | 9/2014 | Bills | G03H 1/0443 356/51 |
| 2015/0192529 A1* | 7/2015 | Sato | G01N 21/88 438/16 |

* cited by examiner

MARKING APPARATUS AND MARKING METHOD FOR DISPLAY PANEL

FIELD OF THE INVENTION

The present invention relates to the field of display technology, and particularly relates to a marking apparatus for a display panel and a marking method for a display panel.

BACKGROUND OF THE INVENTION

In the production process of thin film transistor-liquid crystal displays (TFT-LCDs), it is inevitable to generate numerous defective display panels (for example, with moiré or abnormal pixel points). To reduce defective rate, improve yield rate and reduce loss, engineers need to analyze positions where defects occur on display panels, and usually need to sample and analyze defects. During sampling, engineers need to determine positions where the defects occur at first and then mark the positions.

Specifically, an engineer observes a display panel through a microscope, find a position where a defect occurs on the display panel and then manually marks the position with a marker pen.

However, in the process of manually marking the positions where the defects occur on the display panels to be marked with marker pens, it is found that the accuracy of marking cannot be specifically corrected to a pixel due to too large range of manual marking, and meanwhile, marking is made inconveniently because approximate locations where the defects occur need to be determined with naked eyes through microscopic lens during marking.

SUMMARY OF THE INVENTION

The present invention provides a marking apparatus for a display panel and a marking method for a display panel, which can accurately mark a position where a defect occurs on a display panel.

To achieve the above object, the present invention provides a marking apparatus for a display panel, comprising an image acquiring module, a simulated marking module and a real marking module, wherein the image acquiring module is configured to acquire, on a display panel to be marked, an image of a region containing a position where a defect occurs as a simulated image on which simulated marking is performed, the simulated marking module is configured to draw a simulated marking line in the simulated image to simulatedly mark the position, and the real marking module is configured to draw a real marking line on the display panel to be marked according to the simulated marking line.

For example, the marking apparatus for a display panel further comprises a driving module configured to drive the image acquiring module so as to move it to be above the position where the defect occurs on the display panel to be marked.

For example, the driving module comprises a transverse driving motor, a longitudinal driving motor and a recording unit, wherein the transverse driving motor is configured to drive the image acquiring module to move in a transverse direction, the longitudinal driving motor is configured to drive the image acquiring module to move in a longitudinal direction, and the recording unit is configured to record current coordinates of the image acquiring module and control the transverse driving motor and the longitudinal driving motor to move the image acquiring module to above the position where the defect occurs on the display panel to be marked.

For example, the driving module further comprises a transverse support frame and longitudinal support frames, the transverse support frame being located between the two longitudinal support frames which are arranged oppositely, wherein the transverse driving motor is configured to drive the image acquiring module to move on the transverse support frame, and the longitudinal driving motor is configured to drive the transverse support frame to move on the longitudinal support frames.

For example, the region containing the position where the defect occurs on the display panel to be marked is a region with predetermined size taking the position where the defect occurs as a center.

For example, the real marking module comprises a coordinate acquiring unit, a coordinate processing unit and a marking unit, wherein the coordinate acquiring unit is configured to acquire simulated start coordinates and simulated end coordinates of the simulated marking line in the simulated image, the coordinate processing unit is configured to process the simulated start coordinates and the simulated end coordinates to acquire real start coordinates and real end coordinates on the display panel to be marked corresponding to the simulated start coordinates and the simulated end coordinates, and the marking unit moves from a position of the real start coordinates to a position of the real end coordinates to draw the real marking line.

For example, the marking apparatus for a display panel further comprises a driving module configured to drive the marking unit to move from the position of the real start coordinates to the position of the real end coordinates to draw the real marking line.

For example, the coordinate processing unit comprises a storage subunit and an inquiry subunit, wherein the storage subunit is configured to store a correspondence between the region containing the position where the defect occurs on the simulated image and the region containing the position where the defect occurs on the display panel to be marked and generate a corresponding coordinate correspondence table, and the inquiry subunit searches out the real start coordinates corresponding to the simulated start coordinates and the real end coordinates corresponding to the simulated end coordinates according to the coordinate correspondence table.

For example, the real marking module further comprises an adjustment unit configured to adjust the marking unit to be within a visual field of the image acquiring module while drawing the real marking line.

For example, the adjustment unit comprises a rotary motor and a connection rod, and the rotary motor is configured to move the marking unit to be within the visual field of the image acquiring module through the connection rod while drawing the real marking line.

For example, the real marking module further comprises a lifting unit configured to control the marking unit to rise and fall in a vertical direction.

For example, the marking unit includes a marker pen or a spray gun.

For example, the marking apparatus for a display panel further comprises a base platform configured to place the display panel to be marked thereon.

For example, the image acquiring module comprises an image processing unit configured to enlarge the image, acquired by the image acquiring module, of the region containing the position where the defect occurs, and the enlarged image is used as the simulated image.

For example, the image acquiring module comprises an image generation unit and a plurality of enlarging lenses with different magnification factors, wherein the image generation unit generates, according to light transmitting through the enlarging lenses, the enlarged image of the region containing the position where the defect occurs as the simulated image.

For example, the image acquiring module further comprises a lens switching unit configured to switch the enlarging lens.

For example, the image acquiring module further comprises a strip-shaped support, wherein all the enlarging lenses are fixed on the strip-shaped support in a row, and the lens switching unit is configured to drive the strip-shaped support to move along the length direction of the strip-shaped support, so as to switch the enlarging lens.

The present invention further provides a marking method for a display panel, comprising: acquiring, on a display panel to be marked, an image of a region containing a position where a defect occurs as a simulated image on which simulated marking is performed; drawing an simulated marking line in the simulated image to mark the position where the defect occurs; and drawing a real marking line on the display panel to be marked according to the simulated marking line.

For example, the step of drawing a real marking line on the display panel to be marked according to the simulated marking line comprises: acquiring simulated start coordinates and simulated end coordinates of the simulated marking line in the simulated image; processing the simulated start coordinates and the simulated end coordinates to acquire real start coordinates and real end coordinates corresponding to the simulated start coordinates and the simulated end coordinate, respectively, on the display panel to be marked; and drawing the real marking line from a position of the real start coordinates to a position of the real end coordinates.

For example, the step of acquiring, on a display panel to be marked, an image of a region containing a position where a defect occurs comprises: acquiring an enlarged image of the region containing the position where the defect occurs on the display panel to be marked.

The present invention achieves the beneficial effects as below.

In the marking apparatus for a display panel and the marking method for a display panel provided by the present invention, by drawing an simulated marking line in an image of a region containing a position where a defect occurs on a display panel to be marked, and then automatically drawing a real marking line on the display panel to be marked according to the simulated marking line, accurately marking the position where the defect occurs on the display panel to be marked is realized, and it is convenient for an engineer to accurately locate and sample positions where defects occur in the subsequent analysis process.

DETAILED DESCRIPTION OF THE INVENTION

To make a person skilled in the art better understand the technical solutions of the present invention, a marking apparatus for a display panel and a marking method for a display panel provided by the present invention will be described below in detail with reference to the accompanying drawings.

Embodiment 1

Figure 1:
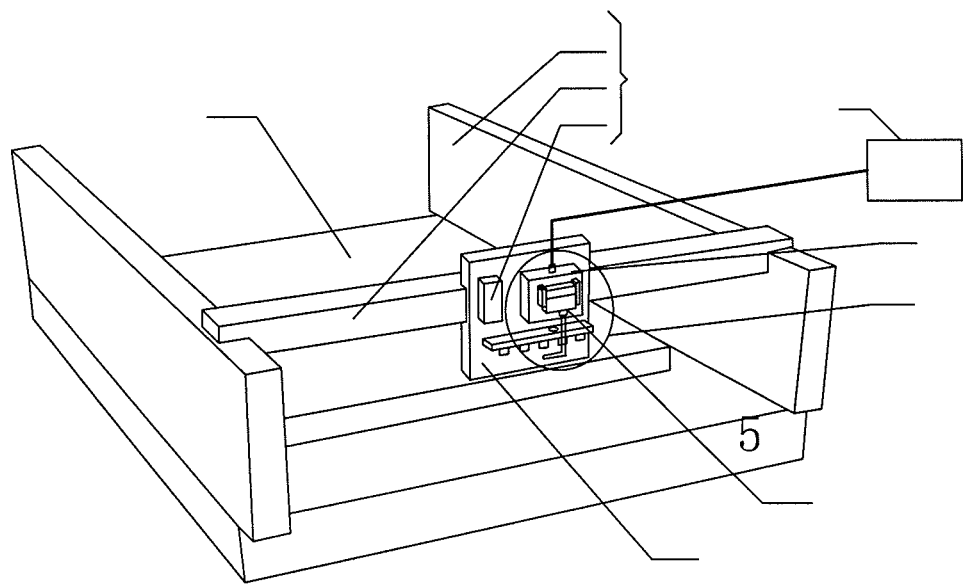
FIG. 1 is a schematic diagram of a structure of a marking apparatus for a display panel provided by Embodiment 1 of the present invention.
Figure 2:
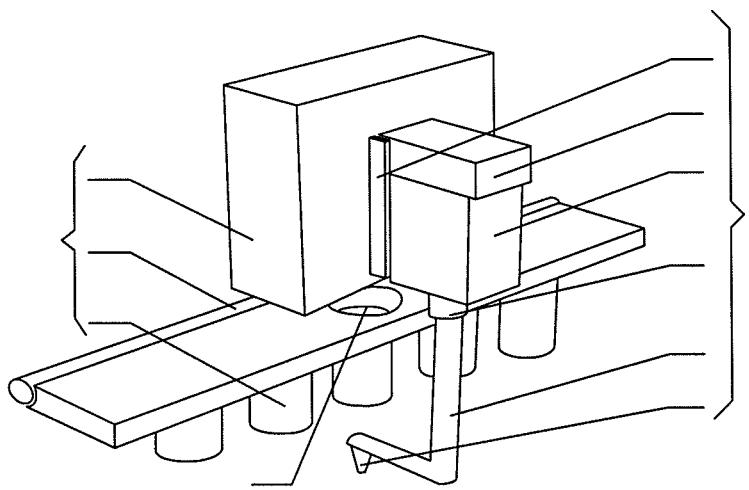
FIG. 2 is an enlarged view of structure Q in FIG. 1.
Figure 3:
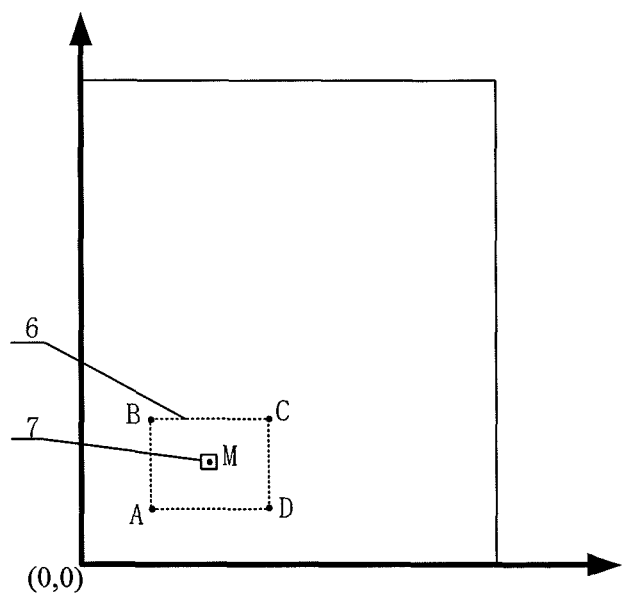
FIG. 3 is a schematic diagram illustrating a coordinate system for a region containing a position where a defect occurs on a display panel to be marked.
Figure 4:
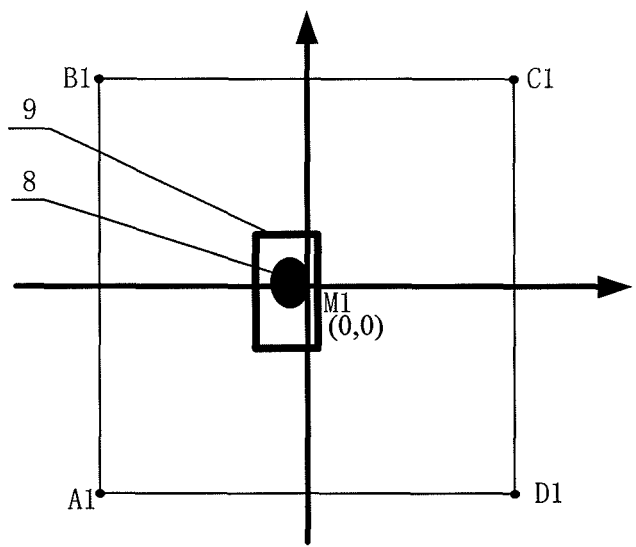
FIG. 4 is a schematic diagram illustrating a coordinate system for the simulated image.

FIG. 1 is a diagram illustrating a structure of a marking apparatus for a display panel provided by Embodiment 1 of the present invention. FIG. 2 is an enlarged view of a structure Q in FIG. 1. FIG. 3 is a schematic diagram of a coordination system for a region containing a position where a defect occurs on a display panel to be marked. FIG. 4 is a schematic diagram of a coordinate system for the simulated image. As shown in FIGS. 1 to 4, the marking apparatus comprises a driving module 1, an image acquiring module 2, a simulated marking module 3 and a real marking module 4. The driving module 1 is connected to the image acquiring module 2, the image acquiring module 2 is connected to the simulated marking module 3, and the simulated marking module 3 is connected to the real marking module 4. The driving module 1 is configured to drive the image acquiring module 2 so as to move it to be above a position 8 where a defect occurs on the display panel 5 to be marked. The image acquiring module 2 is configured to acquire, on the display panel 5 to be marked, an image of a region containing the position 8 where the defect occurs as a simulated image on which simulated marking is performed. The simulated marking module 3 is configured to draw a simulated marking line 9 in the simulated image, so as to simulatedly mark the position 8 where the defect occurs. The real marking module 4 is configured to draw a real marking line 7 on the display panel 5 to be marked according to the simulated marking line 9.

It should be noted that, the connection may be wired or wireless when the image acquiring module 2 is connected to the simulated marking module 3 and the simulated marking module 3 is connected to the real marking module 4.

Here, the image acquiring module 8 may be configured to acquire an image with predetermined size taking the position where the defect occurs as a center on the display panel 5 to be marked and the image is used as the simulated image on which simulated marking is performed. In the technical solutions of the present invention, the image acquiring module 2 acquires the image of the region with predetermined size taking the position where the defect occurs as the center and the image is used as the simulated image on which simulated marking is performed, then the simulated marking module 3 draws a simulated marking line 9 in the simulated image to mark the position 8 where the defect occurs in the simulated image, and the real marking module 4 finally draws a real marking line 7 according to information of the simulated marking line 9, so that the position 8 where the defect occurs on the display panel 5 is marked accurately.

It should be noted that, setting the position 8 where the defect occurs as the center of the simulated image helps an engineer to simulatedly mark and subsequently observe and analyze the position 8 where the defect occurs. In addition, the region 6 with predetermined size indicates that the size of the region on the display panel 5 to be marked corresponding to the image acquired by the image acquiring module 2 is predetermined, and an appropriate predetermined size may be designed correspondingly based on actual demands.

In addition, it also should be noted that a simulated marking should be defined as a pattern formed by line segments or continuous curve in advance.

Optionally, the real marking module 4 comprises a coordinate acquiring unit 402, a coordinate processing unit 403 and a marking unit 406. The coordinate acquiring unit 402 is connected to both the image acquiring module 2 and the coordinate processing unit 403, the coordinate processing unit 403 is connected to the marking unit 406 and located beneath the coordinate acquiring unit 402, and the marking unit 406 is located beneath the coordinate processing unit 403. The coordinate acquiring unit 402 is configured to acquire simulated start coordinates and simulated end coordinates of the simulated marking line 9 in the simulated image. The coordinate processing unit 403 is configured to process the simulated start coordinates and the simulated end coordinates to acquire real start coordinates and real end coordinates corresponding to the simulated start coordinate and the simulated end coordinate, respectively, on the display panel 5 to be marked. The marking unit 406 moves from a position of the real start coordinates to a position of the real end coordinates to draw the real marking line 7. Here, the marking unit 406 includes a marker pen or a spray gun.

After the image of the region 6 with predetermined size taking the position 8 where the defect occurs as the center on the display panel 5 to be marked is acquired, the coordinates of the points in the image may be obtained according to an image processing software, and then the simulated marking module 3 is utilized to simulatedly mark the position 8 where the defect occurs on the image with the simulated marking line 9. The simulated start coordinates and the simulated end coordinates refer to start coordinates and end coordinates of the simulated marking line 9 on the simulated image.

It should be noted that the simulated marking module 3 may comprise an input equipment and a display screen configured to display the image acquired by the image acquiring module 2 as the simulated image on which simulated marking is performed, wherein the input equipment may be a mouse, a touch screen, or the like, and the display screen may be a device having an image display function.

When the input equipment is a mouse, by controlling the movement of the mouse manually, a simulated marking line 9 is drawn on the display screen on which the simulated image is displayed. The coordinate acquiring unit 402 acquires simulated start coordinates and simulated end coordinates of the simulated marking line 9 and uploads the simulated start coordinates and the simulated end coordinates to the coordinate processing unit 403.

When the input equipment is a touch screen, a display screen for displaying the simulated image may be made to be a touch screen. When a touch pen or a finger of a person slides on the touch screen, a simulated marking line 9 may be drawn. The coordinate acquiring unit 402 acquires simulated start coordinates and simulated end coordinates of the simulated marking line 9 and uploads the simulated start coordinates and the simulated end coordinates to the coordinate processing unit 403.

Further, the coordinate processing unit 403 comprises a storage subunit and an inquiry subunit. The inquiry subunit is connected to both the coordinate acquiring unit 402 and the storage subunit. The storage subunit is configured to store a correspondence between the simulated image and the region 6 of the display panel 5 to be marked with predetermined size and generate a corresponding coordinate correspondence table. The inquiry subunit searches out the real start coordinates corresponding to the simulated start coordinates and the real end coordinates corresponding to the simulated end coordinates according to the coordinate correspondence table.

Optionally, the marking apparatus for a display panel further comprises a base platform. While marking the position 8 where defect occurs on the display panel 5 to be marked, the display panel 5 to be marked needs to be placed on the base platform and then the coordinates of the points on the whole display panel 5 to be marked are obtained. The real start coordinates and the real end coordinates refer to start coordinates and end coordinates of the real marking line 7 corresponding to the simulated marking line 9 on the display panel 5 to be marked. The driving module 1 may move the image acquiring module 2 to any position in a horizontal plane of certain height above the display panel 5 to be marked, and also the driving module 1 may acquire a coordinate point corresponding to the image acquiring module 2 on the display panel 5 to be marked. The coordinate point corresponding to the image acquiring module 2 is consistent with the central point of the region 6 with predetermined size and corresponds to the central point of the simulated image.

Optionally, the driving module 1 comprises a transverse support frame 102 and longitudinal support frames 101, a transverse driving motor, a longitudinal driving motor and a recording unit 103. The transverse support frame 102 is located between the two longitudinal support frames 101 which are arranged oppositely. The longitudinal support frames 101 are located at marginal area on two opposite sides of the base platform. The recording unit 103 is connected to the transverse driving motor and the longitudinal driving motor, the transverse driving motor is connected to the image acquiring module 2, and the longitudinal driving motor is connected to the transverse support frame 102. The transverse driving motor is configured to drive the image acquiring module 2 to move on the transverse support frame 102. The longitudinal driving motor is configured to drive the transverse support frame 102 to move on the longitudinal support frames 101. The recording unit 103 is configured to record the current coordinates of the image acquiring module 2, and control the operation of the transverse driving motor and the longitudinal driving motor, so as to move the image acquiring module 2 to above the position 8 where the defect occurs on the display panel 5 to be marked. Through the cooperation of the longitudinal driving motor and the transverse driving motor, the image acquiring module 2 may be moved to any position in the horizontal plane. Optionally, the driving module 1 further comprises a fixation plate 11 connected to the transverse support frame 102, and the image acquiring module 2 is fixed on the fixation plate 11. The transverse driving motor drives the fixation plate 11 to move on the transverse support frame 102, so as to drive the image acquiring module 2 to move in a transverse direction. In order to save space, for example, the recording unit 103 may also be provided on the fixation plate 11.

It should be noted that, the longitudinal driving motor and the transverse driving motor are not shown in figures, and the positional relation between the longitudinal support frames 101 and the base platform is not limited to what is shown in the figures. In addition, the driving module 1 in this embodiment may be of other structures, and the above structure of the driving module 1 does not limit the technical solutions of the present invention.

The process of storing the correspondence between the simulated image and the region 6 of the display panel 5 to be marked with predetermined size and generating the corresponding coordinate correspondence table is described as below in detail in combination with the accompanying drawings.

Referring to FIG. 3, in a real coordinate system, the corresponding coordinates of the image acquiring module 2 on the display panel 5 to be marked are (5, 5), the real coordinates of four corners of the region 6 with predetermined size are point A (4, 4), point B (4, 6), point C (6, 6) and point D (6, 4), respectively, and the coordinates of the central point M of the region 6 with predetermined size are (5, 5). Referring to FIG. 4, in an simulated coordinate system, the real coordinates of four corners of the simulated image are point A1 (−10, −10), point B1 (−10, 10), point C1 (10, 10) and point D (10, −10), respectively, and the coordinates of the central point M1 of the simulated image are (0, 0), wherein point A, point B, point C and point D corresponds to point A1, point B1, point C1 and point D1, respectively, and the central point M of the region 6 with predetermined size corresponds to the central point M1 of the simulated image. It can be seen from the above that the points in the simulated image and the points in the region 6 with predetermined size are in a one-to-one correspondence. It is to be noted that, embodying the above point A, point B, point C, point D, point M, point A1, point B1, point C1, point D1 and point M1 is merely for facilitating understanding the technical solutions of the present invention by the person skilled in the art, and the above correspondence does not limit the technical solutions of the present invention.

After the one-to-one correspondence between the points in the simulated image and the points in the region 6 with predetermined size is determined, the storage subunit may establish a correspondence table of the coordinates of the points in the region 6 with predetermined size and the coordinates of the points in the simulated image according to the correspondence and the real coordinates (acquired by the driving module 1) of the central point of the region 6 with predetermined size. The correspondence table records coordinates (real coordinates) of pixel points on the display panel 5 to be marked corresponding to the coordinates (simulated coordinates) of each point in the simulated image. Therefore, while drawing the real marking line 7 by using the real marking module 4, the position of the real marking line 7 may be corrected to a specific pixel on the display panel 5 to be marked, so that the position 8 where the defect occurs on the display panel 5 to be marked is accurately marked.

It should be noted that, although a correspondence exists between the simulated image and the region 6 with predetermined size, the coordinate correspondence table of the points in the region 6 with predetermined size and the points in the simulated image needs to change with the movement of the region 6 with predetermined size (the change in the coordinates of the central point of the region 6 with predetermined size).

Referring to FIG. 1, the real marking module 4 further comprises an adjustment unit connected to the marking unit 406. The adjustment unit is configured to adjust the marking unit 406 to right below the image acquiring module 2 while drawing the real marking line 7. In the process of searching a position 8 where a defect occurs, generating a simulated image and performing simulated marking, to clearly observe the position 8 where the defect occurs, the real marking module 4 may be disposed outside the visual filed of the image acquiring module 2 at this time. However, while drawing the real marking line 7, the real marking module 4 may be adjusted to beneath the image acquiring module 2 (within the visual field of the image acquiring module 2) by the adjustment unit. At this time, the drawing condition of the real marking line 7 may be observed in real time by the image acquiring module 2. Optionally, the adjustment unit comprises a rotary motor 404 and a connection rod 405. One end of the connection rod 405 is connected to the rotary motor 404, while the other end of the connection rod 405 is connected to the marking unit 406. The rotary motor 404 is configured to rotate the marking unit 406 to right beneath the image acquiring module 406 through the connection rod 405 while drawing the real marking line 7.

In this embodiment, the driving module 1 may be further configured to drive the marking unit 406 to move from a position of the real start coordinates to a position of the real end coordinates to draw the real marking line 7. Here, the real marking module 4 is disposed on the transverse support frame 102 and is driven to move through the operation of the transverse driving motor and the longitudinal driving motor, so as to realize the movement of the marking unit 406 from the position of the real start coordinates to the position of the real end coordinates to draw the real marking line 7.

Before the real marking line 7 is drawn, the adjustment unit adjusts the real marking module 4 to a position of the central point right beneath the image acquiring module 2, so that a marking point of the real marking module 4 coincides with a coordinate point corresponding to the image acquiring module 2 on the display panel to be marked. At this time, the driving module 1 may be used to drive the image acquiring module 2 and the real marking module 4 to move as a whole, so as to draw the corresponding real marking line 7. With the above structure, the marking device of the present invention is not required to be provided with an additional driving module for the real marking module 4, so that the production cost of the marking device is reduced. Certainly, in this embodiment, both the image acquiring module 2 and the real marking module 4 may be fixed on the fixation plate 11, as shown in FIG. 1.

Optionally, the real marking module 4 further comprises a lifting unit 401. The lifting unit 401 is disposed between the image acquiring module 2 and the coordinate processing unit 403, and configured to control the coordinate processing unit 403 to rise and fall in a vertical direction so as to drive the adjustment unit and the marking unit 406 to rise and fall. Taking the marking unit 406 being a marker pen as an example, in the process of searching a position 8 where a defect occurs, generating an simulated image and performing simulated marking, it is required to rise the marker pen to an initial position by using the lifting unit 401 in order to avoid the contact between the marker pen and the display panel 5 to be marked. While drawing the real marking line 7, it is required to drop the marker pen to contact the display panel 5 to be marked by using the lifting unit 401, and the maker pen needs to rise to the initial position after drawing each real marking line 7.

The process of drawing a rectangular marking pattern as shown in FIG. 3 will be described below in detail. To draw the rectangular marking pattern as shown in FIG. 3, four simulated marking lines 9 need to be drawn in the simulated image by using the simulated marking module 3, and four real marking lines 7 are correspondingly drawn on the display panel 5 to be marked by using the real marking module 4. Specifically, after one simulated marking line 9 is drawn, the real marking module 4 may draw a corresponding real marking line 7 on the display panel 5 to be marked. The above process is repeated until all of the four real marking lines 7 are drawn. Or, four simulated marking lines 9 are drawn at first, and then four corresponding real marking lines 7 are drawn on the display panel 5 to be marked by the real marking module 4 based on the time sequence in which the four simulated marking lines 9 are drawn.

Still referring to FIG. 2, the image acquiring module 2 comprises an image generation unit 201, a lens switching motor 202, a strip-shaped support (not shown in FIG. 2) and a plurality of enlarging lenses 203 with different magnification factors. The lens switching motor 202 is connected to the strip-shaped support. All of the lens switching motor 202, the strip-shaped support and the enlarging lenses 203 are located below the image generation unit 201. All of the enlarging lenses 203 are fixed on the strip-shaped support in a row. The image generation unit 201 is configured to generate the simulated image based on light transmitting through the enlarging lens 203.

In this embodiment, the lens switching motor 202 may be fixed on the fixation plate 11. An engineer may drive the strip-shaped support to move along the length direction of the strip-shaped support by using the lens switching motor 202, so that the enlarging lens 203 located beneath an incident port 10 of the image generation unit 201 is moved, so as to achieve the purpose of switching enlarging lenses. Optionally, all of the enlarging lenses 203 may be fixed on an annular support, and the annular support may be driven to be rotated by the lens switching motor 202 to move the enlarging lenses 203 beneath the incident port 10, so that the purpose of switching enlarging lenses is achieved. This situation is not shown in figures. Certainly, the enlarging lenses may also be switched manually without the lens switching motor or the strip-shaped support (or annular support).

In the marking device provided by Embodiment 1 of the present invention, the simulated marking module draws a simulated marking line in a simulated image, the real marking module automatically draws a real marking line on the display panel to be marked according to the simulated marking line, so that a position where a defect occurs on a display panel to be marked is accurately marked, and it is convenient for an engineer to accurately locate and sample the position where the defect occurs in the subsequent analysis process.

Embodiment 2

Figure 5:
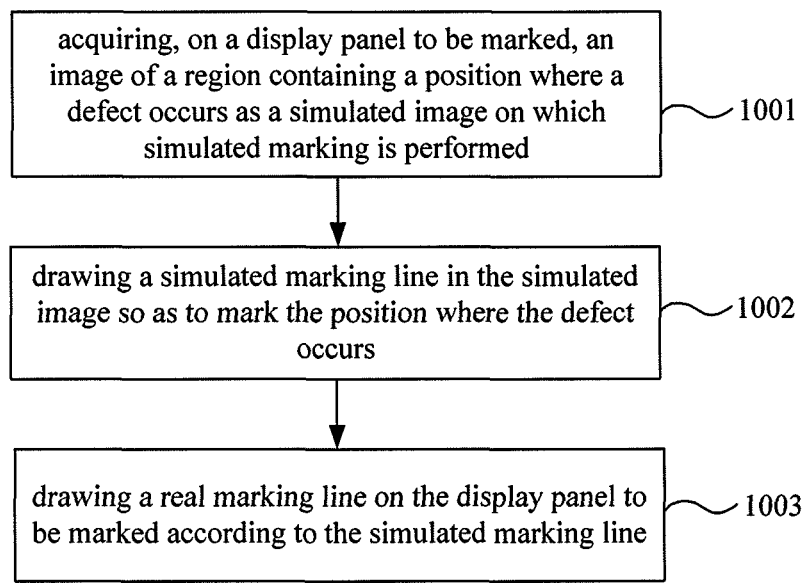
FIG. 5 is a flowchart of a marking method for a display panel provided by Embodiment 2 of the present invention.

FIG. 5 is a flowchart of a marking method for a display panel according to Embodiment 2 of the present invention. As shown in FIG. 5, the marking method comprises the following steps 1001-1003.

Step 1001: on a display panel to be marked, an image of a region containing a position where a defect occurs is acquired as a simulated image on which simulated marking is performed.

Step 1001 may be executed by the above driving module and the image acquiring module. The specific process may refer to the description of the driving module and the image acquiring module in Embodiment 1, and will not be described repeatedly here.

Step 1002: a simulated marking line is drawn in the simulated image.

Step 1002 may be executed by the simulated marking module. The specific process may refer to the description of the simulated marking module in Embodiment 1, and will not be described repeatedly here.

Step 1003: a real marking line is drawn on the display panel to be marked according to the simulated marking line.

Step 1003 may be executed by the real marking module. The specific process may refer to the description of the real marking module in Embodiment 1, and will not be described repeatedly here.

In this case, Step 1003 comprises the following steps 1014-1034.

Step 1014: simulated start coordinates and simulated end coordinates of the simulated marking line in the simulated image are acquired.

Step 1024: The simulated start coordinates and the simulated end coordinates are processed to acquire real start coordinates and real end coordinates on the display panel to be marked corresponding to the simulated start coordinates and the simulated end coordinates, respectively.

In step 1024, the principle and process of acquiring real start coordinates and real end coordinates according to the simulated start coordinates and the simulated end coordinates may refer to the description in Embodiment 1, and will not be described repeatedly here.

Step 1034: the real marking line is drawn from a position of the real start coordinates to a position of the real end coordinates.

In the marking method for a display panel provided by the present invention, by drawing an simulated marking line in an simulated image and then automatically drawing a real marking line on the display panel to be marked according to the simulated marking line, accurately marking a position where a defect occurs on a display panel to be marked is realized, and it is convenient for an engineer to accurately locate and sample the position where the defect occurs in the subsequent analysis process.

It should be appreciated that, the foregoing embodiments are exemplary embodiments merely for describing the principle of the present invention, but the protection scope of the present invention is not limited thereto. A person skill in the art may make various modifications and improvements without departing from the spirit and essence of the present invention. However, these modifications and improvements shall fall into the protection scope of the present invention.

The invention claimed is:

1. A marking apparatus for a display panel, comprising an image acquiring module, a simulated marking module and a real marking module, wherein, the image acquiring module is configured to acquire, on a display panel to be marked, an image of a region containing a position where a defect occurs as an simulated image on which simulated marking is performed;

the simulated marking module is configured to draw a simulated marking line in the simulated image to simulatedly mark the position where the defect occurs;

the real marking module is configured to draw a real marking line on the display panel to be marked according to the simulated marking line, wherein the real marking module comprises a coordinate acquiring unit, a coordinate processing unit and a marking unit, wherein, the coordinate acquiring unit is configured to acquire simulated start coordinates and simulated end coordinates of the simulated marking line in the simulated image;

the coordinate processing unit is configured to process the simulated start coordinates and the simulated end coordinates to acquire real start coordinates and real end coordinates corresponding to the simulated start coordinates and the simulated end coordinates on the display panel to be marked; and the marking unit moves from a position of the real start coordinates to a position of the real end coordinates to draw the real marking line; and wherein the real marking module further comprises an adjustment unit configured to adjust the marking unit to be outside a visual field of the image acquiring module in a process of searching the position where the defect occurs, generating the simulated image and performing the simulated marking, and adjust the marking unit to be within the visual field of the image acquiring module while drawing the real marking line.

2. The marking apparatus for a display panel according to claim 1, further comprising a driving module configured to drive the image acquiring module so as to move it to be above the position where the defect occurs on the display panel to be marked.

3. The marking apparatus for a display panel according to claim 2, wherein the driving module comprises a transverse driving motor, a longitudinal driving motor and a recording unit, wherein, the transverse driving motor is configured to drive the image acquiring module to move in a transverse direction, the longitudinal driving motor is configured to drive the image acquiring module to move in a longitudinal direction, and the recording unit is configured to record the current coordinates of the image acquiring module, and control the transverse driving motor and the longitudinal driving motor to move the image acquiring module to above the position where the defect occurs on the display panel to be marked.

4. The marking apparatus for a display panel according to claim 3, wherein the driving module further comprises a transverse support frame and longitudinal support frames, the transverse support frame being located between the two longitudinal support frames which are arranged oppositely, wherein, the transverse driving motor is configured to drive the image acquiring module to move on the transverse support frame; and the longitudinal driving motor is configured to drive the transverse support frame to move on the longitudinal support frames.

5. The marking apparatus for a display panel according to claim 1, wherein the region containing the position where the defect occurs on the display panel to be marked is a region with predetermined size taking the position where the defect occurs as a center.

6. The marking apparatus for a display panel according to claim 1, further comprising a driving module configured to drive the marking unit to move from the position of the real start coordinates to the position of the real end coordinates to draw the real marking line.

7. The marking apparatus for a display panel according to claim 1, wherein the coordinate processing unit comprises a storage subunit and an inquiry subunit, wherein, the storage subunit is configured to store a correspondence between the simulated image and the region containing the position where the defect occurs on the display panel to be marked and generate a corresponding coordinate correspondence table, and the inquiry subunit searches out the real start coordinates corresponding to the simulated start coordinates and the real end coordinates corresponding to the simulated end coordinates according to the coordinate correspondence table.

8. The marking apparatus for a display panel according to claim 1, wherein the adjustment unit comprises a rotary motor and a connection rod, and the rotary motor is configured to move the marking unit to be outside or within the visual field of the image acquiring module through the connection rod.

9. The marking apparatus for a display panel according to claim 1, wherein the real marking module further comprises a lifting unit configured to control the marking unit to rise and fall in a vertical direction.

10. The marking apparatus for a display panel according to claim 1, wherein the marking unit includes a marker pen or a spray gun.

11. The marking apparatus for a display panel according to claim 1, further comprising a base platform configured to place the display panel to be marked thereon.

12. The marking apparatus for a display panel according to claim 1, wherein the image acquiring module comprises an image processing unit configured to enlarge the image, acquired by the image acquiring module, of the region containing the position where the defect occurs, and use the enlarged image as the simulated image.

13. The marking apparatus for a display panel according to claim 1, wherein the image acquiring module comprises an image generation unit and a plurality of enlarging lenses with different magnification factors, wherein the image generation unit generates, according to light transmitting through the enlarging lens, an enlarged image of the region containing the position where the defect occurs, and the enlarged image is used as the simulated image.

14. The marking apparatus for a display panel according to claim 13, wherein the image acquiring module further comprises a lens switching unit configured to switch the enlarging lens.

15. The marking apparatus for a display panel according to claim 14, wherein the image acquiring module further comprises a strip-shaped support, wherein, all of the enlarging lenses are fixed on the strip-shaped support in a row; and the lens switching unit is configured to drive the strip-shaped support to move along a length direction of the strip-shaped support, so as to switch the enlarging lens.

16. A marking method for a display panel, comprising:

acquiring, on a display panel to be marked, an image of a region containing a position where a defect occurs as an simulated image on which simulated marking is performed;

drawing an simulated marking line in the simulated image to simulatedly mark the defective position;

drawing a real marking line on the display panel to be marked according to the simulated marking line, wherein the step of drawing a real marking line on the display panel to be marked according to the simulated marking line comprises:

acquiring simulated start coordinates and simulated end coordinates of the simulated marking line in the simulated image;

processing the simulated start coordinates and the simulated end coordinates to acquire real start coordinates and real end coordinates on the display panel to be marked corresponding to the simulated start coordinates and the simulated end coordinates; and drawing the real marking line from a position of the real start coordinates to a position of the real end coordinates;

wherein, adjusting a marking unit for drawing the real marking line to be outside a visual field of an image acquiring module for acquiring the image of the region containing the position where the defect occurs in a process of searching the position where the defect occurs, generating the simulated image and performing the simulated marking, and wherein, adjusting the marking unit to be within the visual field of the image acquiring module while drawing the real marking line.

17. The marking method for a display panel according to claim 16, wherein the step of acquiring, on a display panel to be marked, an image of a region containing a position where a defect occurs comprises:

acquiring an enlarged image of the region containing the position where the defect occurs on the display panel to be marked.

* * * * *